(12) United States Patent
Epstein et al.

(10) Patent No.: US 11,607,173 B2
(45) Date of Patent: Mar. 21, 2023

(54) MEDICAL ELECTRODE CONNECTOR FOR PRINTED LEAD WIRES

(71) Applicant: Nikomed USA, Inc., Hatboro, PA (US)

(72) Inventors: Stephen T. Epstein, Newtown, PA (US); John J. Sinisi, Warminster, PA (US)

(73) Assignee: Nikomed USA, Inc., Hatboro, PA (US)

( * ) Notice: Subject to any disclaimer, the term of this patent is extended or adjusted under 35 U.S.C. 154(b) by 364 days.

(21) Appl. No.: 16/882,468

(22) Filed: May 23, 2020

(65) Prior Publication Data
US 2020/0367826 A1 Nov. 26, 2020

Related U.S. Application Data

(60) Provisional application No. 62/852,880, filed on May 24, 2019.

(51) Int. Cl.
*A61B 5/00* (2006.01)
*A61B 5/25* (2021.01)

(52) U.S. Cl.
CPC .............. *A61B 5/6838* (2013.01); *A61B 5/25* (2021.01); *A61B 5/6826* (2013.01); *A61B 2560/04* (2013.01)

(58) Field of Classification Search
USPC ........................................................ 600/386
See application file for complete search history.

(56) References Cited

U.S. PATENT DOCUMENTS

| 3,829,826 A | * | 8/1974 | Brown | H01R 11/22 24/667 |
| 3,842,394 A | * | 10/1974 | Bolduc | A61B 18/16 439/727 |
| 4,304,453 A | * | 12/1981 | Grunwald | A61B 5/274 439/372 |
| 4,702,256 A | * | 10/1987 | Robinson | A61B 5/274 403/111 |
| 4,797,125 A | | 1/1989 | Malana | |
| 4,911,657 A | | 3/1990 | Berlin | |
| 4,915,656 A | | 4/1990 | Alferness | |
| 5,131,854 A | | 7/1992 | Jose et al. | |
| 5,137,475 A | | 8/1992 | Olms | |
| 5,195,523 A | | 3/1993 | Cartmell et al. | |
| 5,209,679 A | | 5/1993 | Quinlan | |
| 5,224,882 A | | 7/1993 | Olms | |
| 5,295,872 A | | 3/1994 | Christensson | |

(Continued)

*Primary Examiner* — Clayton E. LaBalle
*Assistant Examiner* — Warren K Fenwick
(74) *Attorney, Agent, or Firm* — LaMorte & Associates, P.C.

(57) ABSTRACT

A clip assembly for attaching an electrical lead to a medical electrode. The clip assembly has opposing jaws that can be selectively clipped onto a medical electrode. The jaws are opened and closed using handles. A receptacle is disposed in one handle for receiving the electrical lead. Within the receptacle, the electrical lead makes contact with a shaped conductor. The shaped conductor extends into a jaw and contacts the medical electrode. A clamp is integrated into the handle. The clamp is used to selectively press the electrical lead against the shaped conductor in the receptacle. The clamp can be manually tightened and loosened. As such, the electrical lead can be readily attached to, and disconnected from, the clip assembly as needed.

16 Claims, 6 Drawing Sheets

(56) References Cited

U.S. PATENT DOCUMENTS

| | | | |
|---|---|---|---|
| 5,454,739 | A | 10/1995 | Strand |
| 5,624,281 | A | 4/1997 | Christensson |
| 5,934,925 | A | 8/1999 | Tobler et al. |
| 6,062,915 | A | 5/2000 | Costello et al. |
| 6,123,571 | A | 9/2000 | Craft, Jr. |
| 6,152,754 | A | 11/2000 | Gerhardt et al. |
| 6,223,088 | B1 | 4/2001 | Scharnberg et al. |
| 6,416,350 | B1 | 7/2002 | Harting et al. |
| 6,541,756 | B2 | 4/2003 | Schulz et al. |
| 6,780,065 | B2 * | 8/2004 | Schwarz .............. H01R 13/631 439/725 |
| 7,255,609 | B1 | 8/2007 | Epstein |
| 9,225,155 | B1 | 12/2015 | Rauckman et al. |
| 9,408,547 | B2 | 8/2016 | Zhou et al. |
| 9,560,998 | B2 | 2/2017 | Al-Ali et al. |
| 2007/0184682 | A1 | 8/2007 | Gobron |
| 2011/0054286 | A1 | 3/2011 | Crosby |
| 2016/0128600 | A1 | 5/2016 | Su et al. |
| 2016/0338610 | A1 | 11/2016 | Zhou et al. |
| 2017/0258355 | A1 | 9/2017 | Hilz et al. |

\* cited by examiner

MEDICAL ELECTRODE CONNECTOR FOR PRINTED LEAD WIRES

RELATED APPLICATIONS

This application claims the benefit of U.S. provisional application No. 62/852,880, filed May 24, 2019.

BACKGROUND OF THE INVENTION

1. Field of the Invention

In general, the present invention relates to connectors that are used to interconnect wire leads to the snap heads of medical electrodes. More particularly, the present invention relates to connectors that are designed to selectively receive a flat printed wire lead or a traditional wire lead so that the lead can be connected to a medical electrode.

2. Prior Art Description

Many tests, such as electrocardiograms, require that specialized medical electrodes be attached to the body. These medical electrodes typically have metal connectors, commonly called snap heads, that enable a lead wire to be connected to the medical electrode. The snap head is typically engaged with some type of clip, such as an alligator clip, that is connected to a lead wire. The lead wire extends to the medical equipment. As such, the electrode makes electrical contact with the patient, the clip makes electrical contact with the electrode, and the wire lead makes electrical contact between the clamp and the medical equipment.

The electrodes make direct physical contact with a patient's skin. As such, most electrodes are intended for one-time use. That is, they are used on a patient then discarded. This is the primary reason why clips are used to engage the electrodes. The clips can be easily detached from the electrodes, so that the electrodes can be discarded. However, with many types of medical equipment, such as electrocardiogram machines, it is common for the wire leads to contact the skin and clothing of the patient being tested. In many institutions, the lead wires of various medical equipment are reused repeatedly. In addition, the wire leads are not cleaned or sterilized between uses. This practice can cause significant patient cross-contamination.

Wire leads contain significant levels of metal and are therefore relatively expensive components in relation to the disposable electrodes. Likewise, the clip that connects the wire leads to the electrodes are complex assemblies that are relatively expensive in relation to the price of the disposable electrodes. The price of a component is the primary factor in determining if a component is reusable or disposable. In the prior art, there are wire leads that are permanently attached to clips. Such prior art is exemplified by U.S. Pat. No. 4,797,125 to Malana and U.S. Pat. No. 5,137,475 to Olms. Typically, if the clip and wire are joined in a unit, the combined cost of the components causes the assembly to be reused many times, often until component failure, before the assembly is replaced.

In certain prior art products, wire leads connect to clip using male/female plug connectors. This enables the wire leads to be selectively attached to, and detached from, the clips. Such prior art connectors are exemplified by U.S. Pat. No. 6,541,756 to Schulz. The use of male/female plug connectors adds significantly to the cost of manufacturing both the lead wires and the clips. Furthermore, the use of male/female connectors often makes the components impractical to clean and sterilize.

Recently, printed leads have been introduced as a replacement for wire leads. Printed leads are designed for only single use applications. Printed leads have conductive ink that is printed onto a strip of plastic substrate. The printed lead is far less expensive than a traditional metal wire and can be readily thrown away after one use without generating much waste. Printed electrode leads are exemplified by U.S. Patent No. 2011/0054286 to Crosby. A problem that exists in the art is that there are few clip assemblies that are designed to connect to disposable printed leads. The result is that many medical facilities do not want to transition to printed leads, since it requires specialized clip assemblies be purchased that cannot be used with traditional wire leads.

A need therefore exists for an improved clip assembly that is designed to connect to both printed leads and traditional wire leads. A need also exists for an improved clip assembly that is inexpensive enough to justify periodic replacement and robust enough to withstand periodic sterilization. These needs are met by the present invention as described and claimed below.

SUMMARY OF THE INVENTION

The present invention is a clip assembly for attaching an electrical lead to a medical electrode. The electrical lead can be a disposable flat printed lead. The clip assembly has two jaws that can be selectively clipped onto a medical electrode. The jaws include a first jaw and an opposing second jaw that are joined at a pivot connection. The jaws are opened and closed using handles, wherein a first handle and an opposing second handle are also joined by the pivot connection. The clip assembly is configured so that any rotational movement about the pivot connection of the first handle toward the second handle causes rotational movement of the first jaw away from the second jaw.

A receptacle is disposed in said first handle for receiving the electrical lead. The receptacle is sized to receive either a flat printed lead or a traditional wire lead. Within the receptacle, the electrical lead makes contact with a shaped conductor. The shaped conductor extends from the first handle to the first jaw, wherein at least some of the shaped conductor is exposed in the receptacle and along the first jaw.

A clamp is integrated into the first handle. The clamp is used to selectively press the electrical lead against the shaped conductor in the receptacle. The clamp can be manually tightened and loosened. As such, the electrical lead can be readily attached to, and disconnected from, the clip assembly as needed.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention clip assembly can be embodied in many ways, only two exemplary embodiments of the clip assembly are shown. The exemplary embodiments set forth two of the best modes contemplated for the invention. The exemplary embodiments, however, are only examples set forth for the purposes of explanation and discussion. The exemplary embodiments should not be considered limitations when interpreting the scope of the appended claims.

Figure 1:
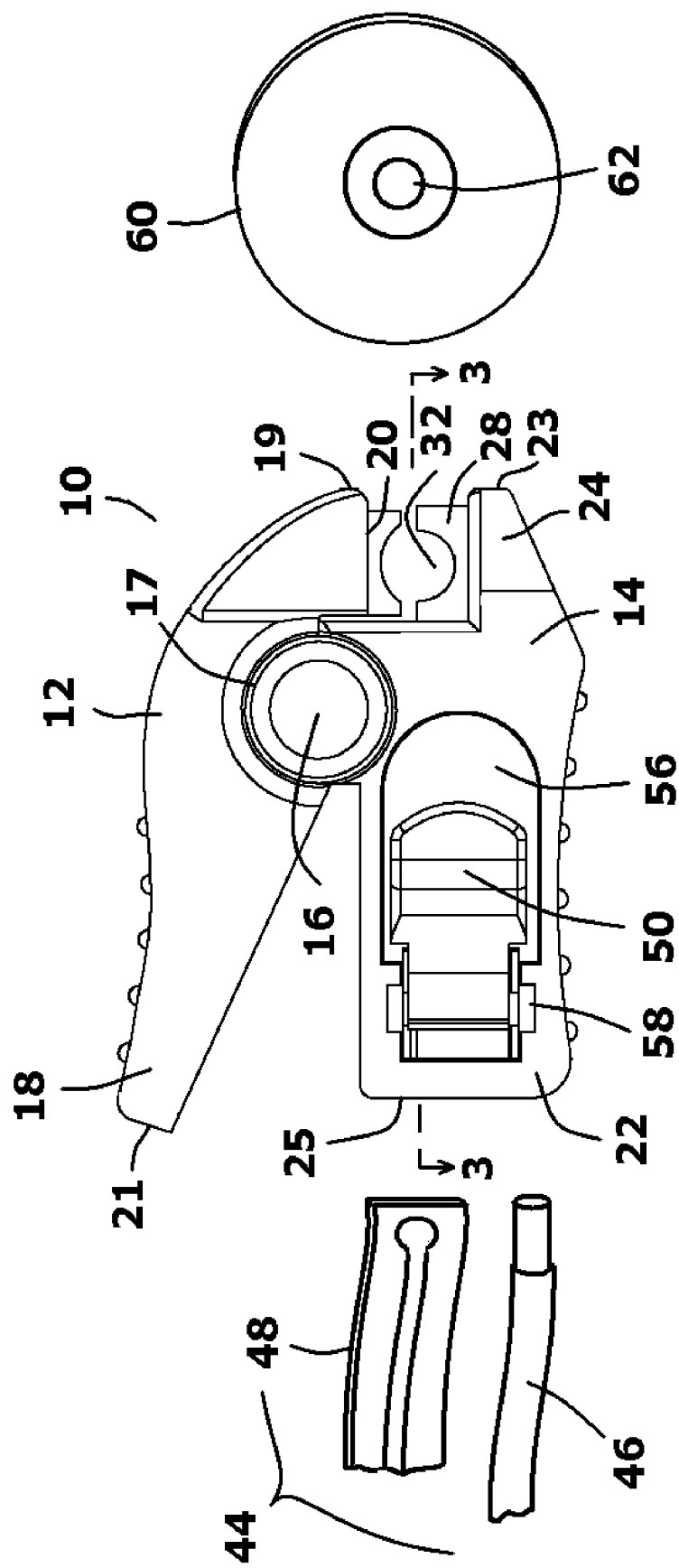
FIG. 1 shows an exemplary embodiment of a clip assembly in accordance with the present invention, shown in conjunction with a segment of two electrical leads and a medical electrode.
Figure 2:
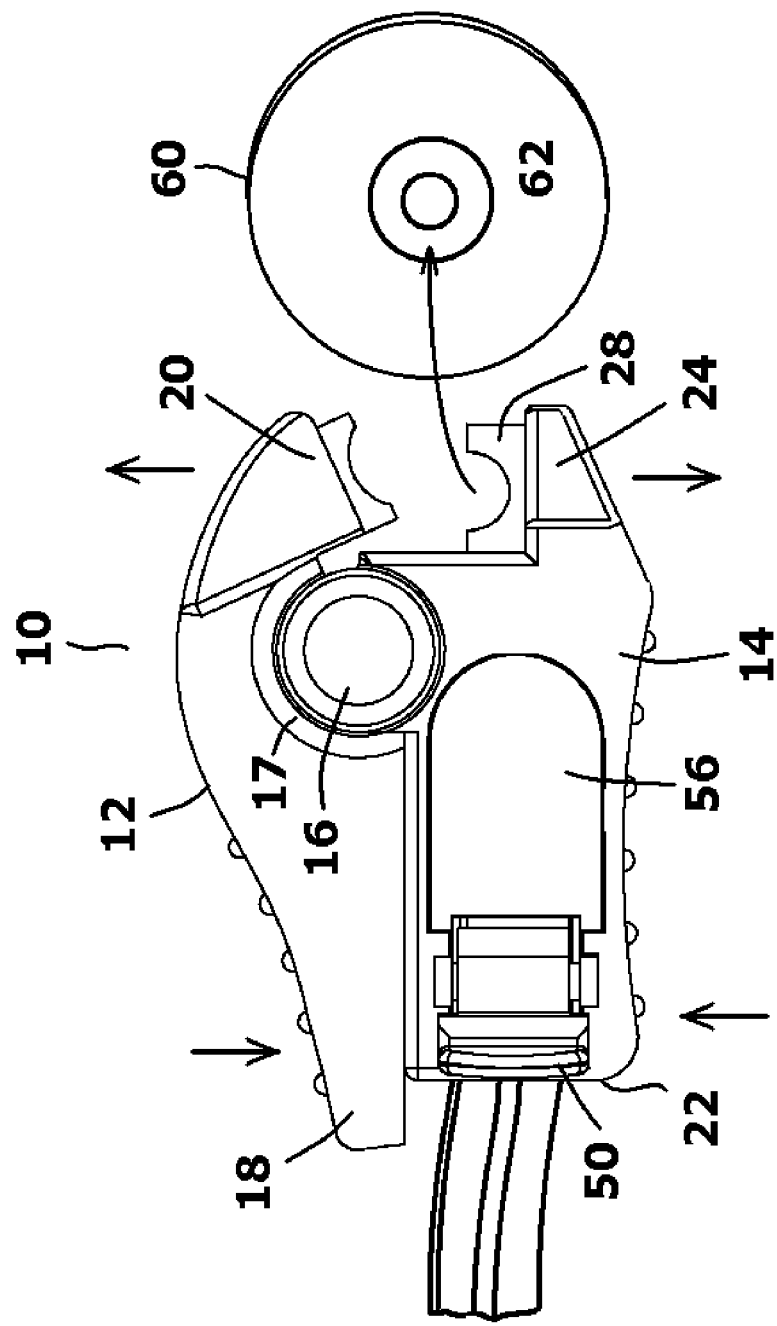
FIG. 2 shows the exemplary embodiment of FIG. 1 with the clip assembly pressed into an open configuration.
Figure 3:
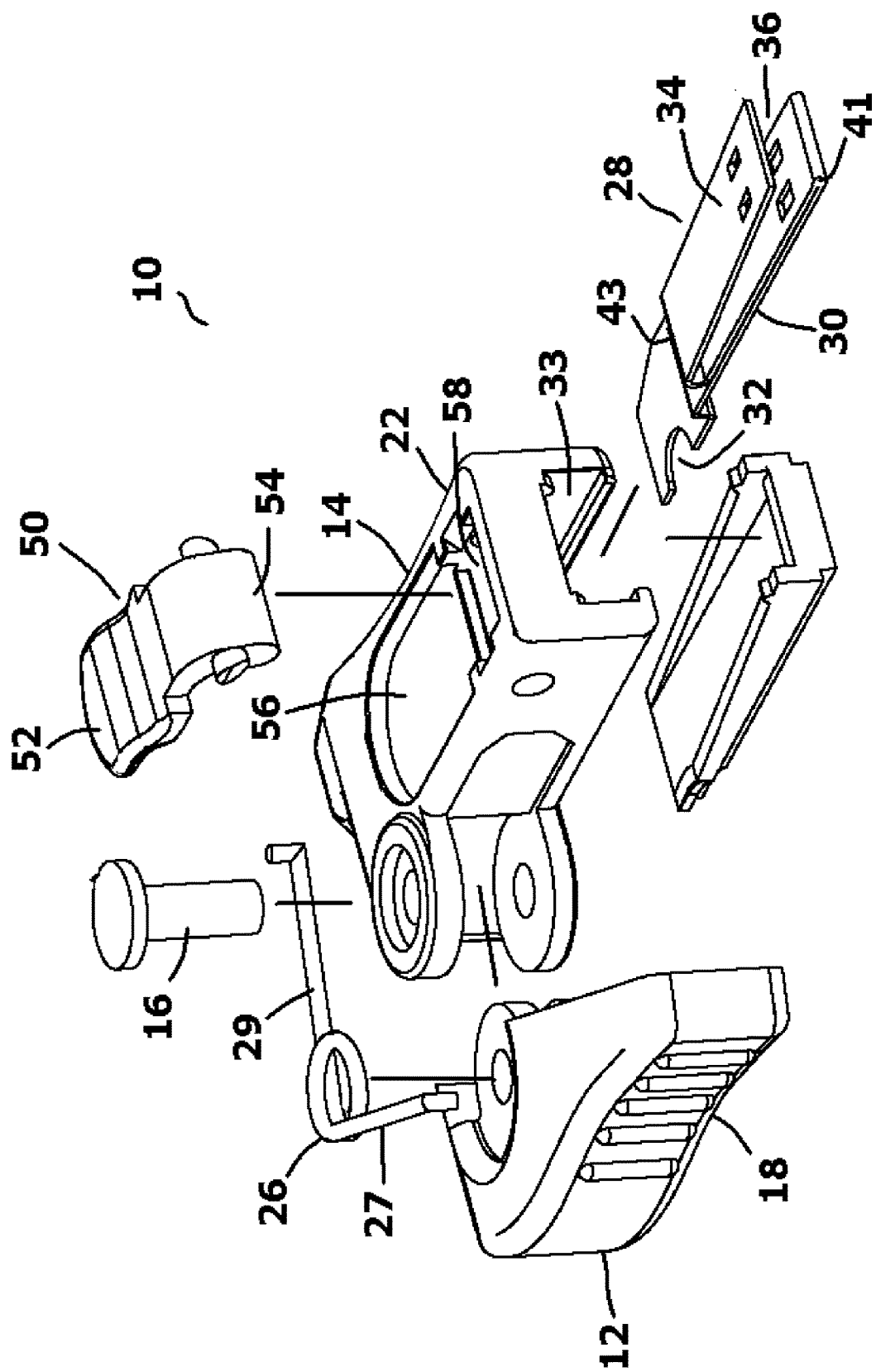
FIG. 3 shows an exploded view of the exemplary embodiment of FIG. 1.

Referring to FIG. 1, FIG. 2 and FIG. 3, a clip assembly 10 is shown. The clip assembly 10 is a spring clip, with an upper section 12 and a lower section 14. The upper section 12 and the lower section 14 are preferably separate molded pieces made from a dielectric plastic. The upper section 12 and the lower section 14 are joined together by a pivot pin 16. The pivot pin 16 joins the upper section 12 and the lower section 14 at a pivot connection 17, therein joining the upper section 12 and the lower section 14 together in a clip configuration.

The upper section 12 has a first end 19 and an opposite second end 21. The upper section 12 has an upper handle 18 that extends from the second end 21 to the pivot connection 17. The upper section 12 also has an upper jaw 20 that extends from the pivot connection 17 to the first end 19 of the upper section 12. The lower section 14 also has a first end 23 and an opposite second end 25. The lower section 14 has a lower handle 22 that extends from the second end 25 to the pivot connection 17. The lower section 14 also has a lower jaw 24 that extends from the pivot connection 17 to the first end 23. A torsion spring 26 is provided that is centered around the pivot pin 16. The torsion spring 26 has a first arm 27 that engages the upper section 12 and a second arm 29 that engages the lower section 14. The torsion spring 26 biases the upper jaw 20 and the lower jaw 24 toward each other. The upper jaw 20 and the lower jaw 24 can be separated by squeezing together the upper handle 18 and the lower handle 22 in opposition to the bias of the torsion spring 26.

A receptacle 33 is formed in the lower handle 22. The receptacle 33 is elongated. The receptacle 33 has a length that is long enough to receive a printed lead 48 and is wide enough to accommodate a wire lead 46. In this manner, either a printed lead 48 or a wire lead 46 can be advanced into the receptacle 33. A shaped conductor 28 is provided. Part of the shaped conductor 28 is disposed within the receptacle 33. The shaped conductor 28 is formed from copper, aluminum or some other highly conductive metal or metal alloy. The shaped conductor 28 has a straight section 30. The straight section 30 extends from the receptacle 33 in the lower handle 22 to the lower jaw 24. Within the lower jaw 24, the shaped conductor 28 terminates with a semicircular depression 32. The semicircular depression 32 is used for engaging a snap head of a medical electrode, as is later explained.

Within the receptacle 33, the shaped conductor 28 has an inclined section 34 that extends from the straight section 30. The inclined section 34 extends away from the straight section 30 due to serpentine bends 41, 43 in the metal forming the inclined section 34. The second bend 43 that forms the inclined section 34 has a spring constant that biases the inclined section 34 at an incline but enables the inclined section 34 to be temporarily pressed flat against the straight section 30. When the inclined section 34 is in its inclined configuration, a wedge-shaped receiving area 36 exists between the inclined section 34 and the straight section 30. The receiving area 36 is open and accessible through the second end 25 of the lower handle 22. The receiving area 36 is sized to receive and engage an electrical lead 44. The electrical lead 44 can be either a traditional wire lead 46 or a specialized disposable printed lead 48.

Figure 4:
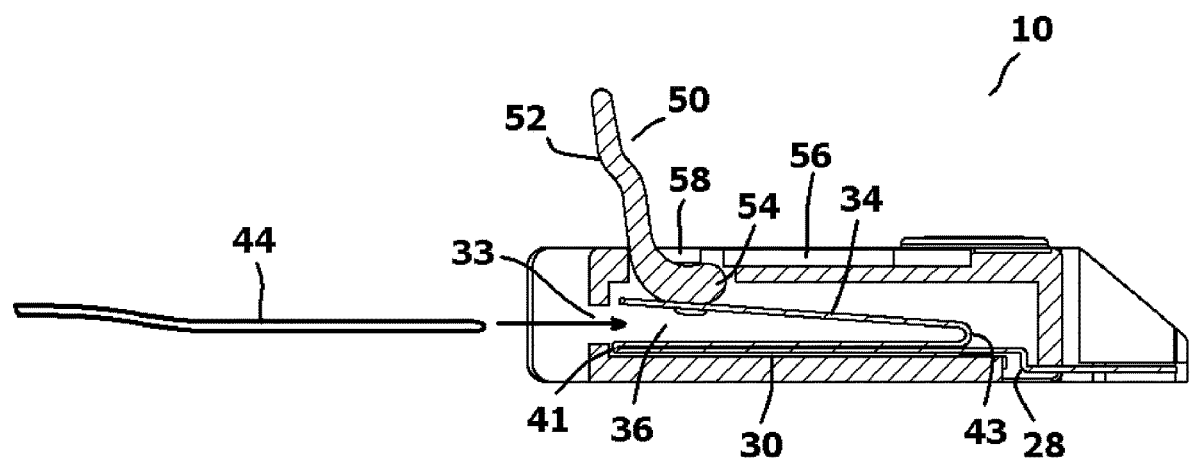
FIG. 4 is a cross-sectional view of the embodiment of FIG. 1 viewed along view line 3-3 with the receptacle clamp in an open condition.
Figure 5:
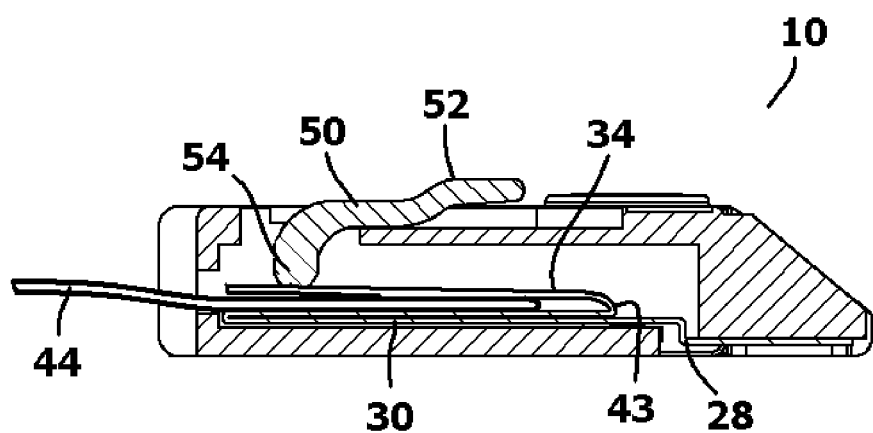
FIG. 5 is a cross-sectional view of the embodiment of FIG. 1 viewed along view line 3-3 with the receptacle clamp in a locked condition.

Referring to FIG. 4 and FIG. 5 in conjunction with FIGS. 1, 2 and 3, it can be seen that a clamp in the form of a cam lever 50 is provided. The cam lever 50 is attached to the lower handle 22. The cam lever 50 has a finger tab 52 and a cam head 54. The cam lever 50 has a pivot connection to the lower handle 22. A relief 56 is formed in the lower handle 22 to receive the cam lever 50. An opening 58 is formed in the relief 56 to accommodate the cam head 54. When the finger tab 52 of the cam lever 50 is rotated, the cam head 54 extends through the opening 58 and advances into the receptacle area 36 within the lower handle 22. The cam head 54 contacts the inclined section 34 of the shaped conductor 28 and moves the inclined section 34 toward the straight section 30. This closes the receiving area 36 and clamps any electrical lead 44 that may be placed within the receiving area 36.

In order to utilize the clip assembly 10, an electrical lead 44 is affixed to the clip assembly 10. This is achieved by placing an electrical lead 44 into the receiving area 36 within the receptacle 33 and manually manipulating the cam lever 50. The cam lever 50 clamps the inclined section 34 against the electrical lead 44, wherein the electrical lead 44 becomes interposed between the inclined section 34 of the shaped conductor 28 and the straight section 30 of the shaped conductor 28. Both contacted surfaces are conductive. As such, the orientation of the electrical lead 44 is not relevant. This is important if a printed lead 48 is used, that may only be conductive on one side. Once attached, the clip assembly 10 is squeezed open and clamped onto a snap head 62 of a medical electrode 60. Once released, the semicircular depression 32 adjacent the lower jaw 24, contacts the medical electrode 60, therein completing electrical continuity between the electrical lead 44 and the medical electrode 60.

Figure 6:
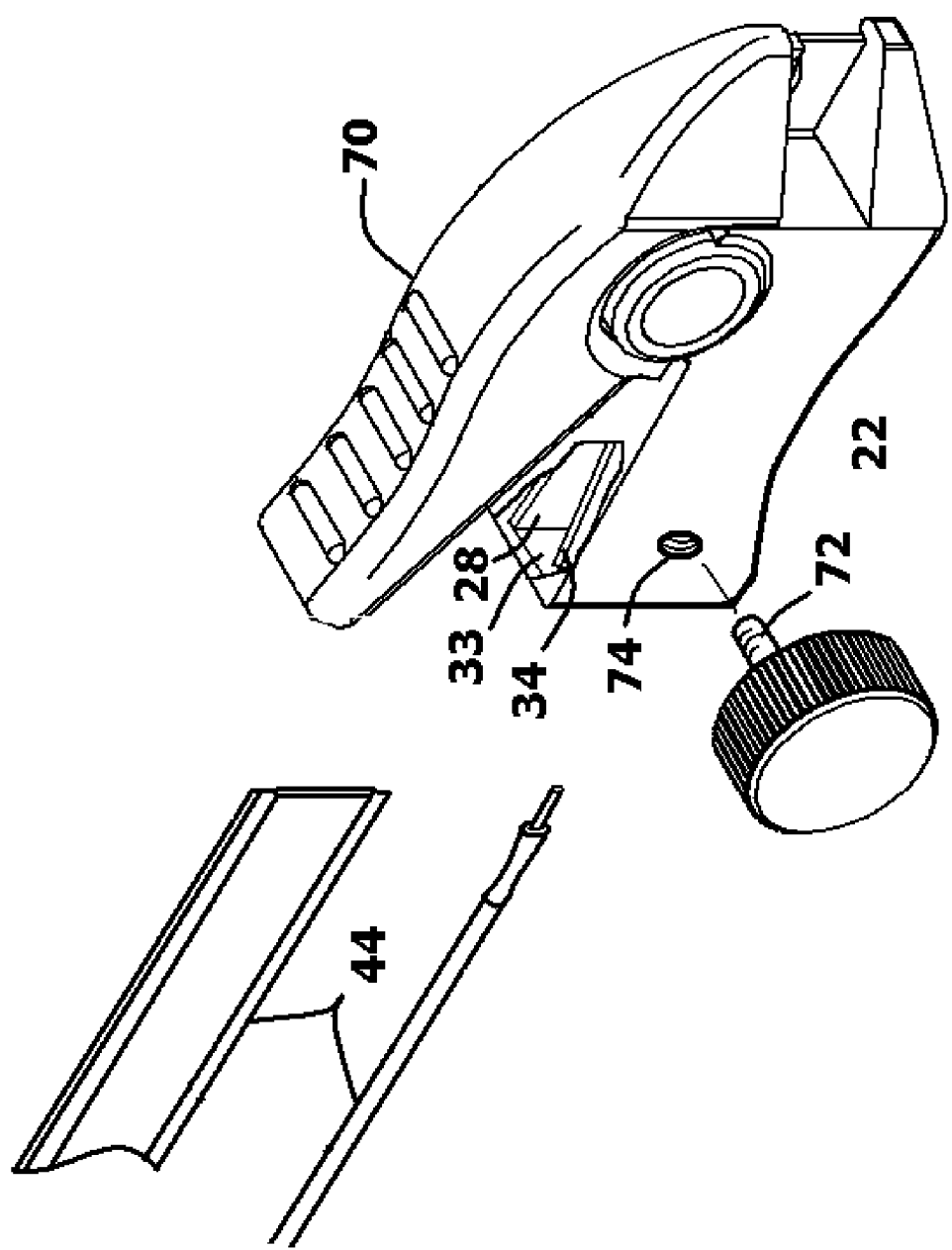
FIG. 6 shows an alternate exemplary embodiment for the clip assembly.

Referring to FIG. 6, an alternate embodiment of a clip assembly 70 is shown. In this embodiment, the clamp used to engage an electrical lead 44 is altered. All other components are the same and are referenced using the same numbers as were used in the first embodiment. In this embodiment, the cam lever of the earlier embodiment is replaced with a threaded bolt 72. The threaded bolt 72 passes through a threaded hole 74 in the lower handle 22. The threaded bolt 72 enters the receptacle 33 and contacts the inclined section 34 of the shaped connector 28. By tightening and loosening the threaded bolt 72, the inclined section 34 can be selectively clamped against an electrical lead 44. As such, the electrical lead 44 can be clamped in placed, or released, depending upon the manipulation of the threaded bolt 72.

It will be understood that the embodiments of the present invention that are illustrated and described are merely exemplary and that a person skilled in the art can make many variations to those embodiments. All such embodiments are intended to be included within the scope of the present invention as defined by the appended claims.

What is claimed is:

1. A clip assembly for attaching an electrical lead to a medical electrode, said clip assembly comprising:
- a first jaw and an opposing second jaw joined at a pivot connection;
- a first handle and an opposing second handle joined by said pivot connection, wherein rotational movement about said pivot connection of said first handle toward said second handle causes rotational movement of said first jaw away from said second jaw;
- a receptacle disposed in said first handle for receiving said electrical lead;
- a shaped conductor that extends from said first handle to said first jaw, wherein at least some of said shaped conductor is exposed in said receptacle and along said first jaw;
- a clamp for selectively pressing said electrical lead against said shaped conductor in said receptacle, wherein said clamp can be manually tightened and loosened.

2. The assembly according to claim 1, further including a spring that biases said first jaw toward said second jaw.

3. The assembly according to claim 1, wherein said shaped conductor includes a straight section in said receptacle and an inclined section that extends from said straight section within said receptacle, wherein said clamp selectively deforms said inclined section against said straight section.

4. The assembly according to claim 3, wherein said shaped conductor is a single metal element that is bent to form said inclined section and said straight section.

5. The assembly according to claim 1, wherein said clamp includes a cam lever that is attached to said first handle.

6. The assembly according to claim 1, wherein said clamp includes a threaded bolt that extends into said receptacle through a threaded hole in said first handle.

7. The assembly according to claim 1, wherein said first jaw and said first handle are molded as a single unit.

8. The assembly according to claim 7, wherein said second jaw and said second handle are molded as a single unit.

9. The assembly according to claim 1, wherein said shaped conductor is a metal element that extends from said first handle to said first jaw, wherein said shaped conductor has a section that protrudes from said first jaw toward said second jaw.

10. The assembly according to claim 9, wherein said section of said shaped conductor that protrudes from said first jaw contains a semicircular depression.

11. A clip assembly for attaching an electrical lead to a medical electrode, said clip assembly comprising:
- opposing jaws joined at a pivot connection;
- opposing handles joined by said pivot connection, wherein relative movement between said opposing handles causes opposite movement in said opposing jaws;
- a receptacle disposed in one of said handles for receiving said electrical lead;
- a shaped conductor that extends from said receptacle to one of said opposing jaws;
- a clamp for biasing said electrical lead against said shaped conductor within said receptacle, wherein said clamp can be manually opened and closed.

12. The assembly according to claim 11, further including a spring that biases said opposing jaws together.

13. The assembly according to claim 11, wherein said shaped conductor includes two spaced sections within said receptacle that can be selectively clamped closed by said clamp.

14. The assembly according to claim 13, wherein said shaped conductor is a single metal element that is bent to form said two spaced sections.

15. The assembly according to claim 11, wherein said clamp includes a cam lever.

16. The assembly according to claim 11, wherein said clamp includes a threaded bolt that extends into said receptacle through a threaded hole.

\* \* \* \* \*